United States Patent

Brattesani

(10) Patent No.: US 6,544,036 B1
(45) Date of Patent: Apr. 8, 2003

(54) ILLUMINATING DENTAL/MEDICAL EXAMINATION MIRROR

(76) Inventor: Steven J. Brattesani, 3309 Fillmore St., San Francisco, CA (US) 94123

( * ) Notice: Subject to any disclaimer, the term of this patent is extended or adjusted under 35 U.S.C. 154(b) by 0 days.

(21) Appl. No.: 09/596,177

(22) Filed: Jun. 16, 2000

(51) Int. Cl.[7] .............................. A61B 1/24; A61C 1/00; A61C 3/00
(52) U.S. Cl. ........................... 433/30; 433/29; 600/241
(58) Field of Search .............................. 433/29, 30, 31; 600/241

(56) References Cited

U.S. PATENT DOCUMENTS

| 3,309,274 A | | 3/1967 | Brilliant | |
|---|---|---|---|---|
| 3,638,013 A | * | 1/1972 | Keller | 433/31 |
| 4,090,506 A | * | 5/1978 | Pilgrim | 433/31 |
| 4,279,594 A | * | 7/1981 | Rigutto | 433/31 |
| 5,139,420 A | * | 8/1992 | Walker | 433/31 |
| 5,139,421 A | | 8/1992 | Verderber | |

FOREIGN PATENT DOCUMENTS

| DE | 1932912 | 1/1971 |
|---|---|---|
| DE | 9308067 | 8/1993 |
| DE | 19807196 | 8/1999 |
| FR | 2749498 | 12/1997 |

* cited by examiner

Primary Examiner—Nicholas D. Lucchesi
(74) Attorney, Agent, or Firm—John P. O'Banion (57) ABSTRACT

An illuminated examination mirror having a neck and angled head with a mirror that is at least partially encircled by light emitting surfaces which direct light to a common point above the surface of the mirror, thereby concentrating the available light for examination. The illuminated examination mirror may be manufactured as a head assembly which may be connected or integrated into a source of illumination, such as a battery powered or fixed illumination source.

44 Claims, 8 Drawing Sheets

ILLUMINATING DENTAL/MEDICAL EXAMINATION MIRROR

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This invention pertains generally to medical/dental examination mirrors, and more particularly to an illuminating mirror used in combination with a light source.

2. Description of the Background Art

Direct observation is often prescribed within dental and medical procedures to enhance diagnostic ability and accuracy of procedures. Often the area to be observed is not accessible for direct viewing and illumination, for example a large portion of the dental surfaces and gums within the oral cavity of a dental patient. Examination mirrors have thereby been used to provide a mechanism for indirect, reflected, viewing.

Examination mirrors, such as a dental mirror, are typically small circular mirrors affixed at an angle to one end of an elongate handle. The dental mirror is positioned in the mouth of the patient so as to reflect an image of the tooth back to the eye of the dentist. It will be appreciated that the clarity and usefulness of the reflected image viewed by the dentist is dependent in part upon the relative amount of ambient light within the oral cavity, however, typical mirrors do not provide a source of illumination.

To increase the amount of light in the mouth, a conventional dental lamp is generally positioned overhead to direct light into the mouth of the patient. However, the hands and head of the dentist as well as dental implements may come between the dental lamp and the mouth of the patient thereby blocking the rays of light, causing the appearance of shadows and otherwise interfering with the reflection from the dental mirror. To avoid these problems, the overhead dental lamp must be constantly positioned and repositioned which requires hand contact with the lamp by the dentist or assistant which can lead to cross-contamination of patients. A variety of handle covers for the overhead lamp have been devised to minimize the possibility of cross-contamination. The patient is also required to open the mouth as wide as possible to maximize the available light which may cause discomfort to patients and in particular those patients suffering with temporal-mandibular joint deficiencies.

In addition, regardless of positioning, the eyes of the patient are exposed to direct high intensity light from the overhead lamp due to the relative proximity of the eyes to the oral cavity being examined. The repetitive repositioning of the dental lamp also increases the time it takes the dentist to complete each dental procedure, reducing the total number of patients that can be seen by the dentist in a day.

Attempts in the prior art to avoid these problems include directing a beam of light from a light source attached to the handle onto the angled dental mirror to illuminate portions of the oral cavity. However, the intense reflected light reduces the reflective surface of the mirror available for view as well as being uncomfortable and interfering with the vision of the dentist.

Furthermore, light sources attached to the handle or fiber optic cables attached to the handle of the dental instrument have the disadvantage of reducing the maneuverability of the instrument in relation to the patient. Such combinations may be relatively heavy and difficult to manipulate by the dentist.

Other combinations employ a portion of the reflective mirror partially or completely removed having a light source contained below the surface of the mirror to provide illumination, such dental mirrors are necessarily large, while they generate heat. These types of dental mirrors have the disadvantage of being hard to sterilize and are expensive and difficult to manufacture in comparison with conventional mirrors. A further disadvantage of these "through the mirror light sources" is the accompanying reduction of viewing area which may be further impeded by the divergent light emitted from the mirror surface. Reduced viewing area and/or the large head size of these instruments increases the number of adjustments made by the dentist during a given procedure thereby extending the length of the procedure. In addition, the light provided by these illumination sources diverges upon emission from the mirror and the amount of directed light is reduced rather than concentrated.

Accordingly, a need exists for an inexpensive illuminating mouth mirror that can efficiently concentrate light to a desired examination area, such as at a spot within the oral cavity of a patient, without causing patient discomfort or obscuring the view of the practitioner. The present invention satisfies that need, as well as others, and generally overcomes the deficiencies found in existing equipment.

BRIEF SUMMARY OF THE INVENTION

The present invention is an illuminated examination mirror for medical and dental procedures which provides concentrated light to enhance the visibility of a subject area viewed by a practitioner utilizing the mirror. The illuminated examination mirror of the present invention may be manufactured as a mirror head for connection to a light source, or as a head portion of a one-piece examination mirror which contains a light-source. One principle drawback of prior lighted examination mirrors is that the emitted light is not concentrated above the plane of the reflective surface of the mirror, and so is not focused on the subject area of the mirror. The apparatus of the present invention concentrates the light and thereby provides more effective illumination with a given amount of light energy while eliminating the need to use external light sources that expose the practitioner and patient to harsh light which is not easily directed to the subject area.

By way of example, and not of limitation, the invention includes an angled head with an elongate neck which may be operably connected to a light source. The angled head and at least a portion of the elongate neck are capable of conducting light from the source of illumination. The angled head surrounds a portion of the outer periphery of the mirror to angularly direct light generally for convergence above the plane of the mirror.

The light source can be a battery powered pen light type light source which is portable and easily maneuverable. The light source may also be a conventional fiber optic light source which is fixed, such as an ISO connector. The present invention is also adapted so that light may be conducted in the visible and non-visible wavelengths to suit a variety of examination applications. For example, fluorescent dyes may be used to disclose plaque when exposed to light of specific wavelengths. Likewise, photocurable orthodontic adhesives and dental composites are cured by exposure to ultraviolet or visible light at optimal wavelengths. The illuminating mirrors of the present invention can fit adaptors of both battery operated, ISO connector, tethered and non-tether corded systems and handpieces to allow the transmission of essentially any wavelength of light from virtually any desired source of illumination.

An object of the invention is to efficiently illuminate a subject area being viewed by an examination mirror without exposing the face or eyes of the patient to harsh overhead light.

Another object of the invention is to provide an illuminating examination mirror that can concentrate light at a point above the reflecting surface of the mirror.

Another object of the invention is to provide an illuminating examination mirror that may adapted to operate with a variety of illumination sources.

Another object of the invention is to provide an illuminating examination mirror that can be manufactured as a disposable illuminating mirror head that can be discarded after a single use to avoid cross-contamination of patients.

Another object of the invention is to provide a device that facilitates efficient examination by illuminating a subject area without interfering with the reflected view accorded the practitioner.

Another object of the invention is to provide an illuminating examination mirror that can direct light into subject areas having minimal access without the necessity of enlarging the access to the subject area for illumination purposes.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus generally shown in FIG. 1 through FIG. 17, where like reference numbers denote like parts. It will be appreciated that the apparatus may vary as to configuration and as to details of the parts without departing from the basic inventive concepts disclosed herein.

Figure 1:
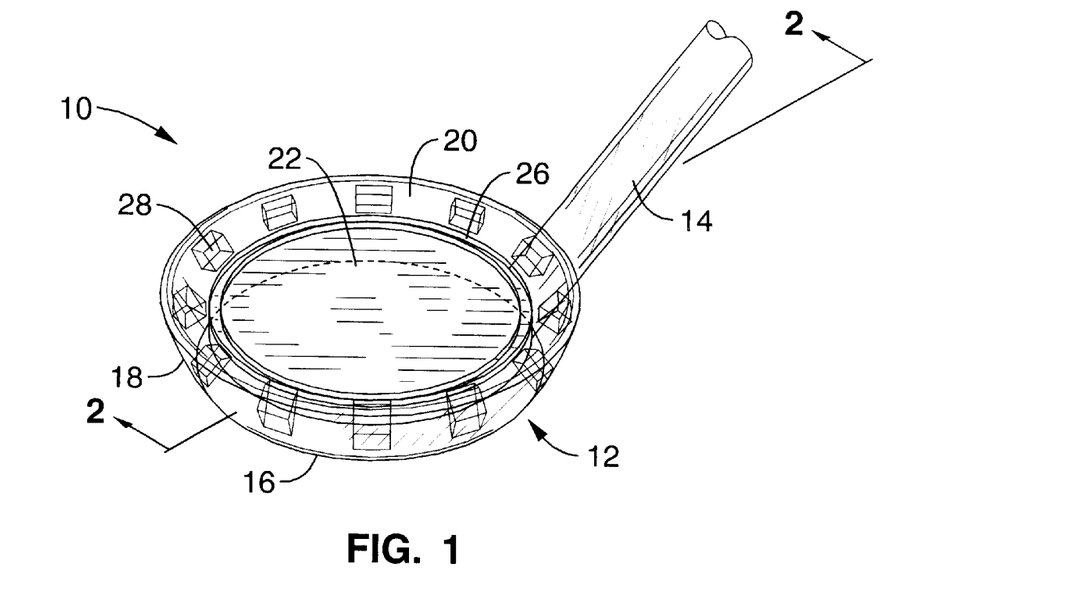
FIG. 1 is a perspective view of an illuminated examination mirror according to the present invention, shown with the neck attached on the underside of the head assembly.
Figure 2:
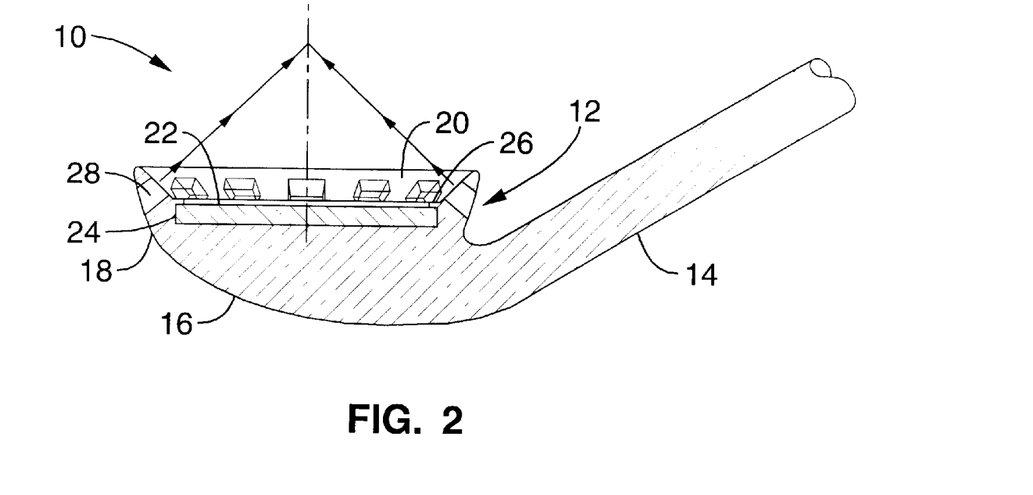
FIG. 2 is a cross-section of the illuminated mirror of FIG. 1 taken through line 2—2.

In FIG. 1 an illuminating examination mirror 10 in accordance with the present invention is shown having a head 12, and a protruding neck 14 which is attached to the bottom surface 16 of the head 12. FIG. 2 illustrates a cross-section of the illuminated examination mirror wherein the edges 18 of the head form a ridge with an interior light emitting surface 20 which is adapted to pass light that has traveled through the neck 14 and head 12 which is directed to converge toward the subject area. A circular mirror 22 of glass, or plastic, is attached to the head and surrounded by the edges 18 of the head. The edge 24 of the mirror 22 is shown retained by a retention lip 26, although it may alternatively be retained with other retention mechanisms such as mechanical fastening or adhesives. A plurality of optional saliva slots 28 within the head are shown positioned about the mirror to prevent liquid accumulation on the surface of mirror 22 retained by the ridged edge 18 of the head 12. The neck 14 is preferably attached at an oblique angle to the plane of the head 12 to simplify positioning the mirror to view the intended subject area. Head 12 and neck 14 are preferably made of a material, such as Lexan®, which are capable of transmitting the desired wavelength of light. It will be understood that the overall shape of head 12, mirror 22, and the position of light emitting surface 20 can follow a variety of polygonal shapes, while the mirror 22 itself may be convex, concave or planar. In addition, the light emitting surface may be apportioned into separate emitting surfaces around the mirror perimeter which are individually capable of emitting the conducted light to the subject area.

It can be seen that the light emitting surface 20 is positioned at an angle such that the emitted light rays are generally directed perpendicularly to the surface of emitting surface 20 that focuses the rays to converge at a distance (preferably in the range of 0.5 to 2.0 inches) above the surface of the mirror which illuminates the subject area as viewed through the mirror by the practitioner.

Prior to use, the light-conductive neck 14 of the illuminated examination mirror 10 is operably connected to any of a variety of illumination sources capable of producing visible or non-visible light (spread spectrum or monochromatic) which may include light at visible, infrared, and/or ultraviolet wavelengths. The light source may be a pen light or optical fiber type light source known in the art. The illumination is transmitted through the neck 14 to the head 12 along the curved path and is emitted at the emitting surface 20 which is focused a specific distance above the surface of the mirror 22. It will be recognized that the invention generally constrains the light in a manner of a light-pipe, as found within the combined neck 14 and head 12, within a given range of light incidence with the exterior surfaces, such that providing smooth transitions reduces the amount of illumination which is lost and unavailable for being directed toward the subject area. Portions of the exterior of the examination mirror may be further configured with reflective treatments at transition areas to reduce the amount of unrecoverable light energy. The light emitting areas are optimally provided as smooth surfaces orthogonal to the path of incident light travel. The user positions the examination mirror to get the best view of the subject area which generally will coincide with the highest light intensity near the focal point of the light while the reflection of the subject area is viewed from mirror 22. The mirror 22 may also be removed whereupon the head may be utilized solely for illumination.

Figure 3:
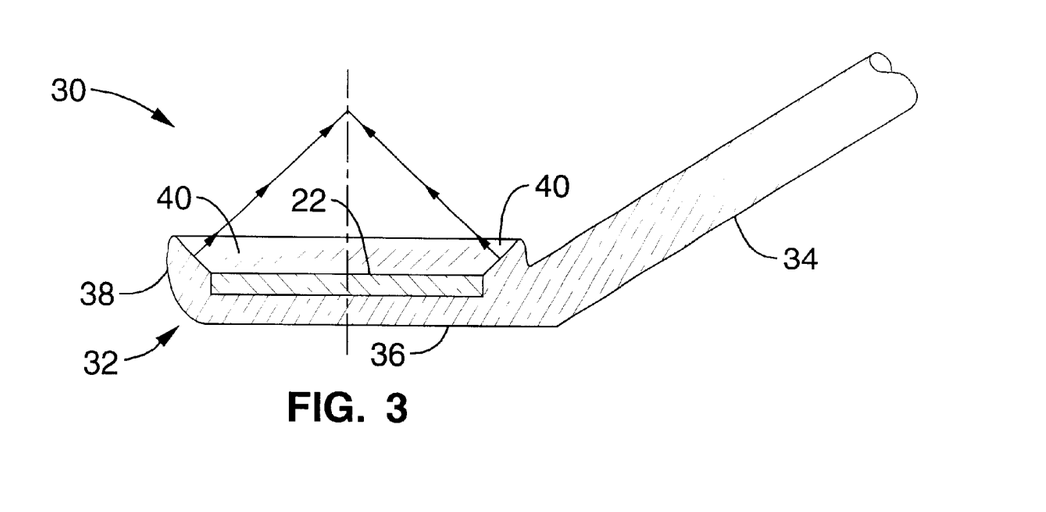
FIG. 3 is a cross-section of an embodiment of an illuminated mirror according to the present invention having a side-attached neck.

FIG. 3 is another embodiment 30 of the illuminated examination mirror having a mirror 22 retained in a substantially planar head 32 having a side attached neck 34. The backside 36 of the head 32 is of less depth than in the head of FIG. 1 which allows the examination mirror 30 of FIG. 3 to be used in tighter spaces, however, the even dispersion of emitted light may be affected. The edges 38 of the head 32 have a similar inside light emitting surface 40 which directs light to converge near the subject area.

Figure 4:
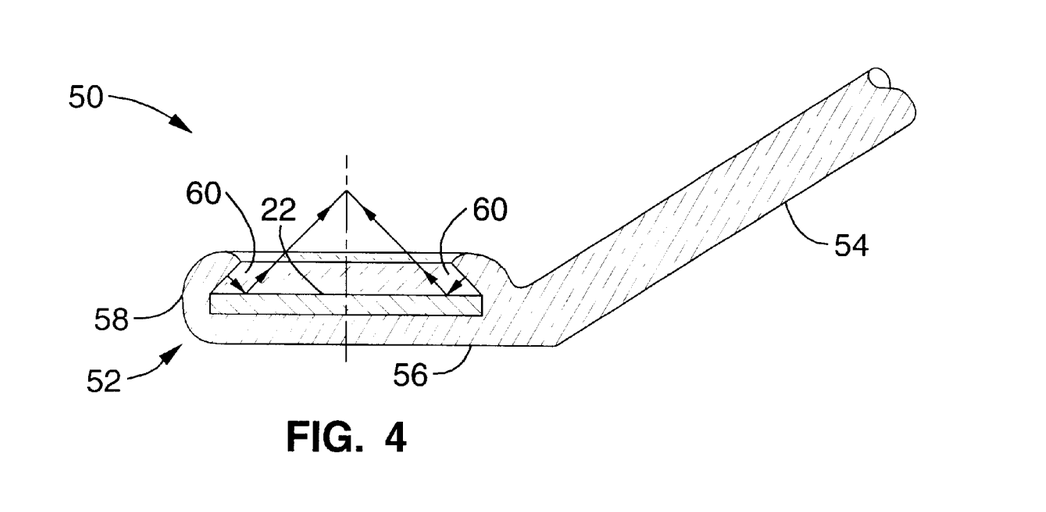
FIG. 4 is a cross-section of an embodiment of an illuminated mirror of the present invention which directs emitted light to reflect from the mirror surface to a focal point above the mirror.

Another embodiment of an illuminating examination mirror 50, is shown in FIG. 4 having a mirror 22 retained within a head 52 having a side attached neck 54, a backside 56 and an edge 58. The light emitting surface 60 of the head 52 is directed toward the plane of mirror 22 wherein the emitted light is directed at an angle to converge on the subject area as shown by the arrowed lead lines. By way of example and not of limitation, the light emitting surface 60 can be positioned at an angle of 45° from the horizontal surface of mirror 22.

Figure 5:
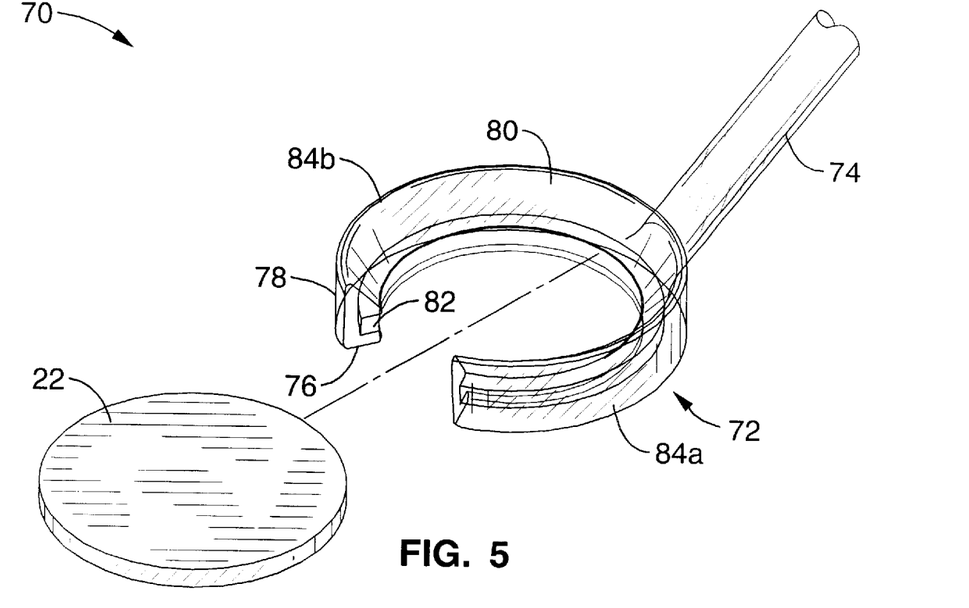
FIG. 5 is an exploded view of an embodiment of an illuminated mirror according to the present invention which has a detachable mirror shown separated from the head.
Figure 6:
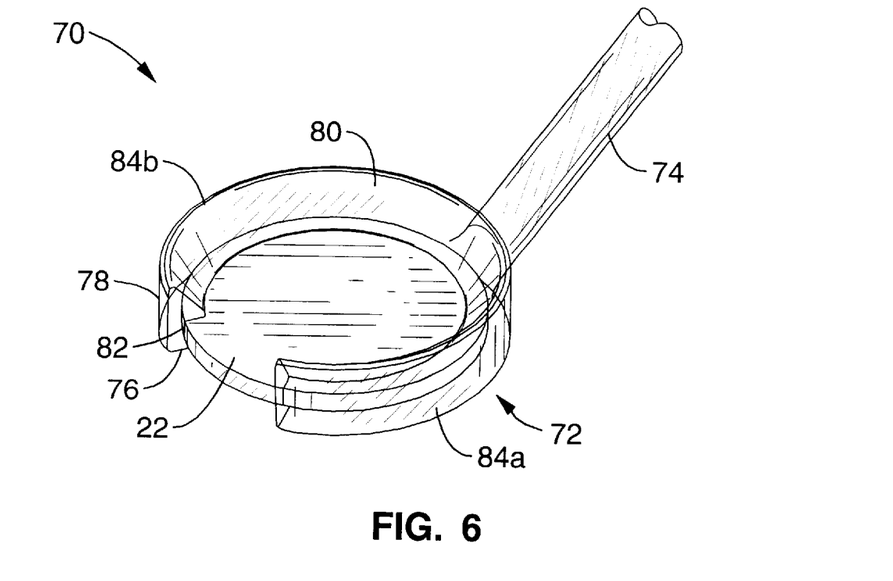
FIG. 6 is a perspective view of the illuminating mirror of FIG. 5, shown assembled.
Figure 7:
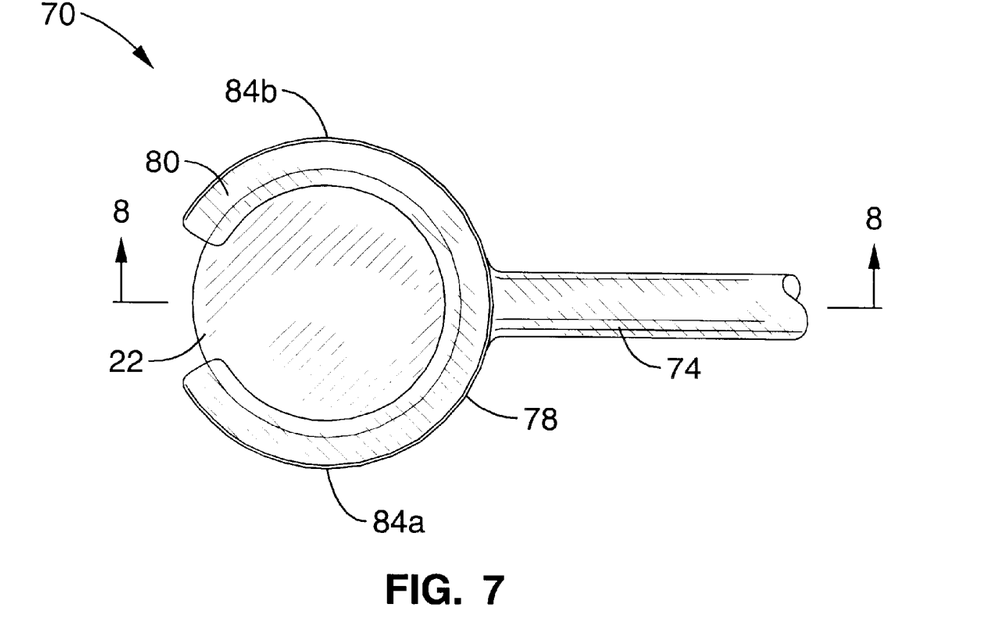
FIG. 7 is a top view of the illuminating mirror of FIG. 6.
Figure 8:
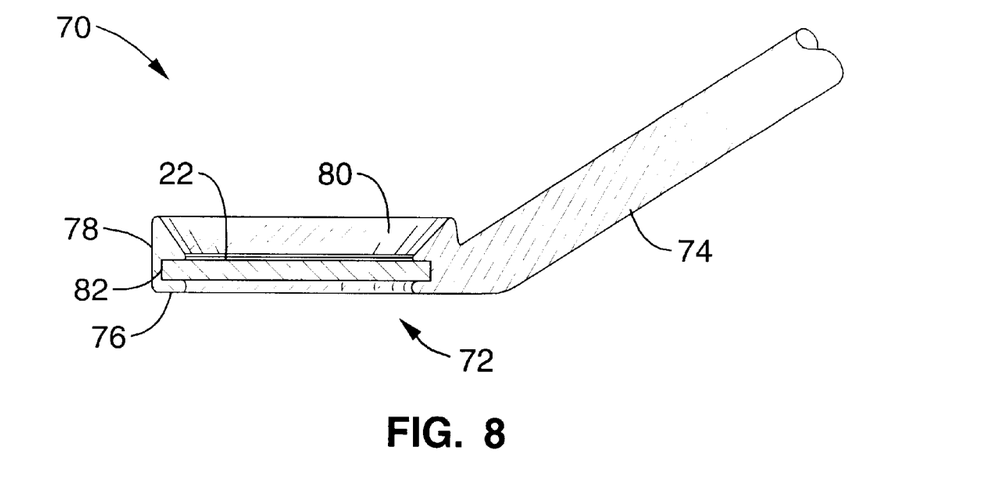
FIG. 8 is a cross-section of the illuminated mirror of FIG. 7 taken through line 7—7.

Another embodiment is an illuminating examination mirror 70 shown in FIG. 5 through FIG. 8 having a removable mirror. FIG. 5 illustrates the mirror 22 separated from the head 72. Neck 74 is attached to the side of head 72 and has a bottom surface 76, an edge 78, an inner light emitting surface 80 and a slot 82. The head 72 has two arcuate arms 84a, 84b which reside within the same plane in a "horseshoe" like configuration wherein the mirror 22 is received and firmly engaged within slot 82. FIG. 6 through FIG. 8 illustrate the assembled examination mirror. It will be appreciated that light within this embodiment will also be emitted from the distal ends of arms 84a, 84b. As an alternative, the emitting surfaces 80 may direct the light at the mirror surface for focused reflection on the subject area (not shown).

Figure 9:
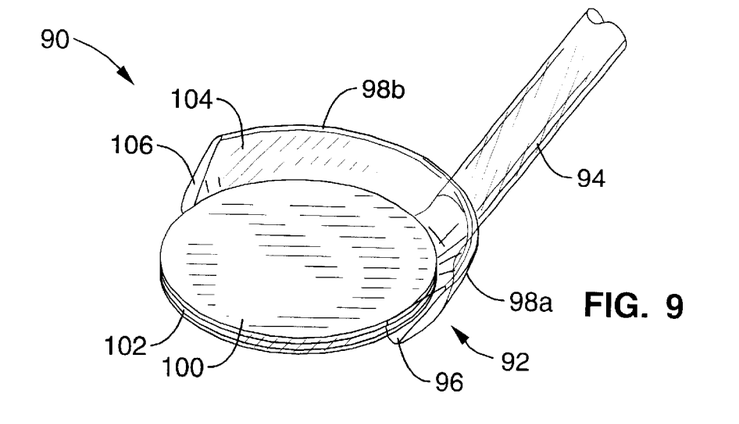
FIG. 9 is a perspective view of an embodiment of an illuminated mirror according to the present invention having a detachable mirror which is partially surrounded by illumination surfaces of the head.
Figure 10:
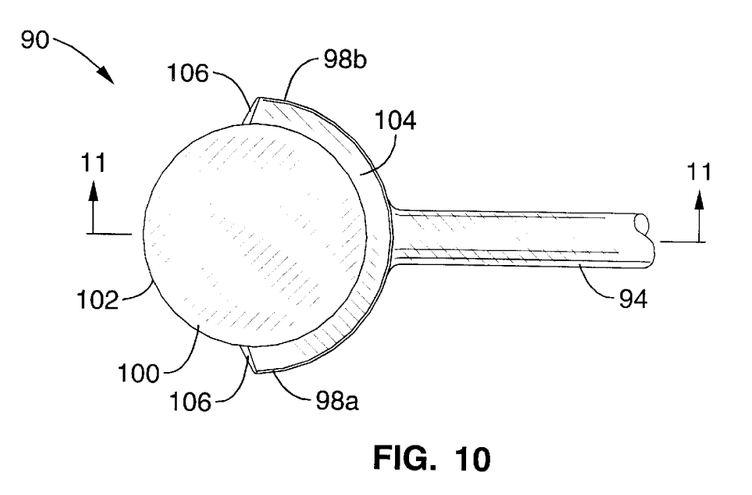
FIG. 10 is a top view of the embodiment shown in FIG. 9.
Figure 11:
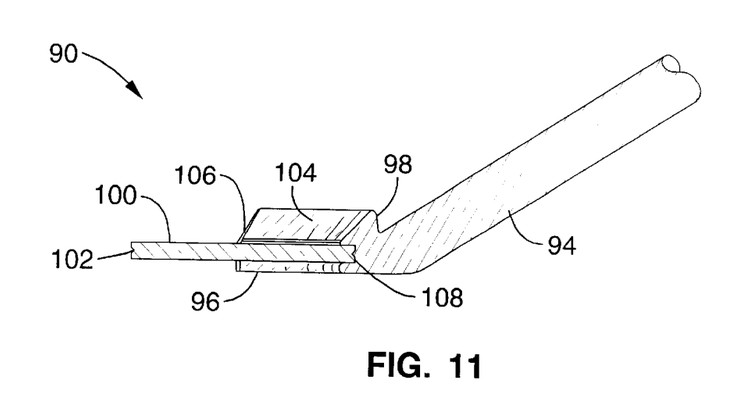
FIG. 11 is a cross-section of the embodiment of FIG. 10 taken through line 11—11.

Another embodiment is an illuminating examination mirror 90 of FIG. 9 through FIG. 11, which provides a partial-ring light emission surface. The examination mirror 90 has an angled head 92 connected with a neck 94. The head 92 has a lower surface 96 and arms 98a, 98b that form an arcuate section for retaining a mirror 100. The mirror 100 has an edge 102 adapted with an annular groove for retention within the head 92. An inner surface 104 of the arms 98a, 98b extends above the surface of the mirror which is preferable beveled 106 to eliminate sharp protrusions. The arms 98a, 98b contain a ridged slot 108 to accommodate the insertion and firm retention of the mirror 100 having an edge 102 with a corresponding groove. The top surface of arms 98a, 98b has an angled light emitting surface 104 which focuses light on the subject area above the surface of mirror 100. An advantage of the partial ring illuminated mirror is the ability to place the unencircled edge of the mirror close to a subject area for close-up viewing. It will be understood that the amount of light being directed to the subject area, for a given light source intensity, is subject to a decrease which may be acceptable for a particular application. The portion of the mirror perimeter which contains the light emitting surface, or surfaces, should be at least 10% within any application so as to provide sufficient light directed and focused on the subject area.

Figure 12:
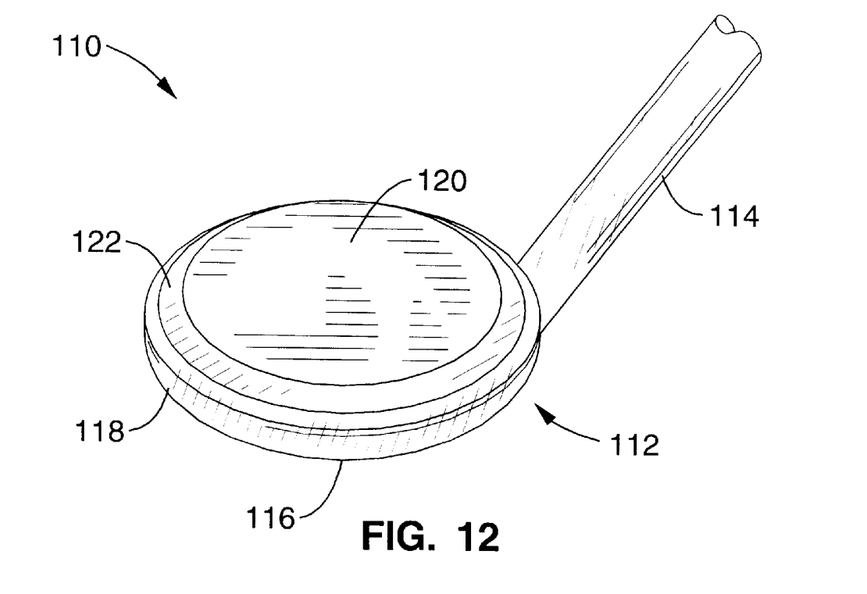
FIG. 12 is a perspective view of an embodiment of an illuminated mirror according to the present invention utilizing a front-surfaced mirror with beveled edges.
Figure 13:
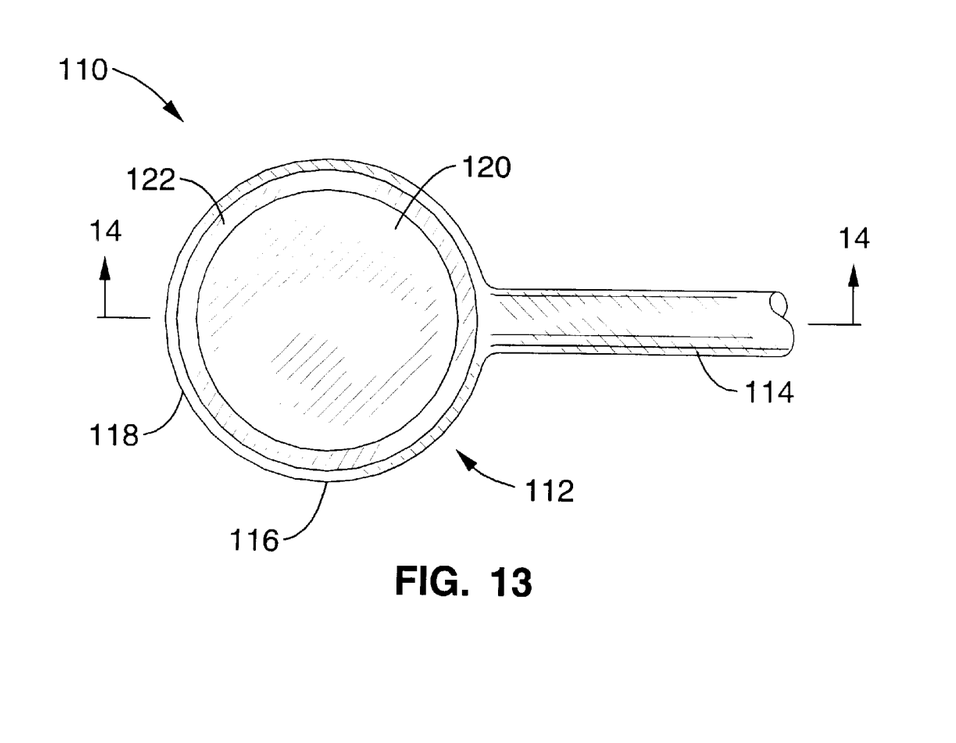
FIG. 13 is a top view of the illuminated mirror of FIG. 12.
Figure 14:
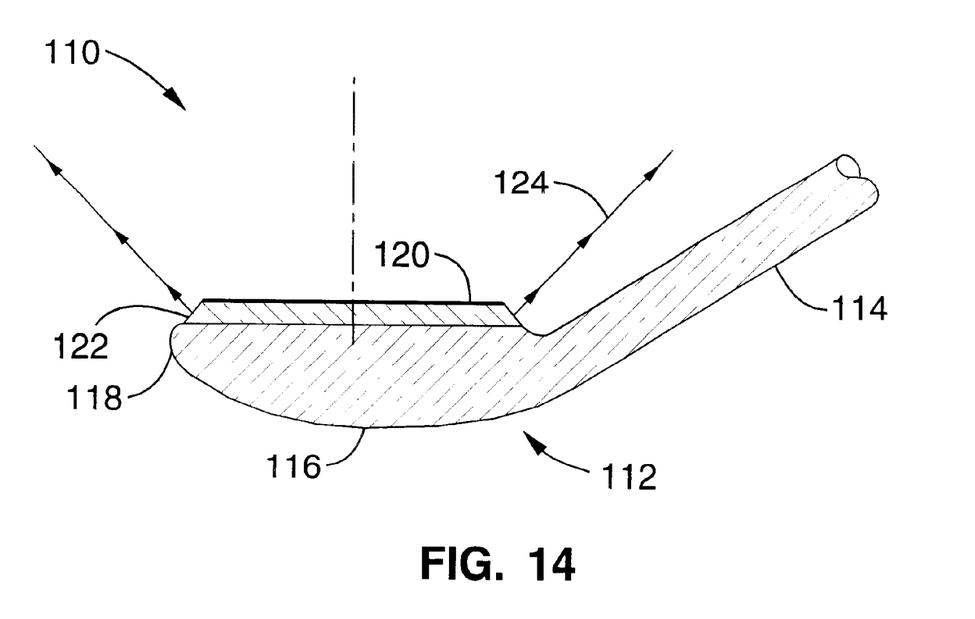
FIG. 14 is a cross-section of the illuminating mirror of FIG. 13 taken through line 13—13.

Another embodiment is an illuminating examination mirror 110 of FIG. 12 through FIG. 14, which provides a beveled front-surfaced mirror as a light emission surface for the light directed from the neck through the head. The examination mirror 110 has a head 112 connected with a neck 114, bottom surface 116, and edge 118. A typical mirror contains a silvered surface against the back-surface of the glass, whereas the light rays being reflected traverse the glass toward the silvering and then traverse the glass again upon reflection. A front-surfaced mirror, by contrast, has a reflective surface on the exterior surface of the glass whereby the light of the incident and reflecting image need not traverse the glass. The mirror 120 is a front-surfaced mirror whose perimeter 122 has been beveled at an angle. Since the silvering is contained on the front-surface of the mirror, the beveling removes the silvering along the perimeter. Light transmitted through the examination head is thereby directed through the emissive surface created by the bevel around the perimeter 122 of the mirror. It will be recognized that the light emitted is not focused on the subject area as in the prior embodiments as the beveled surface directs the light outwardly 124.

Figure 15:
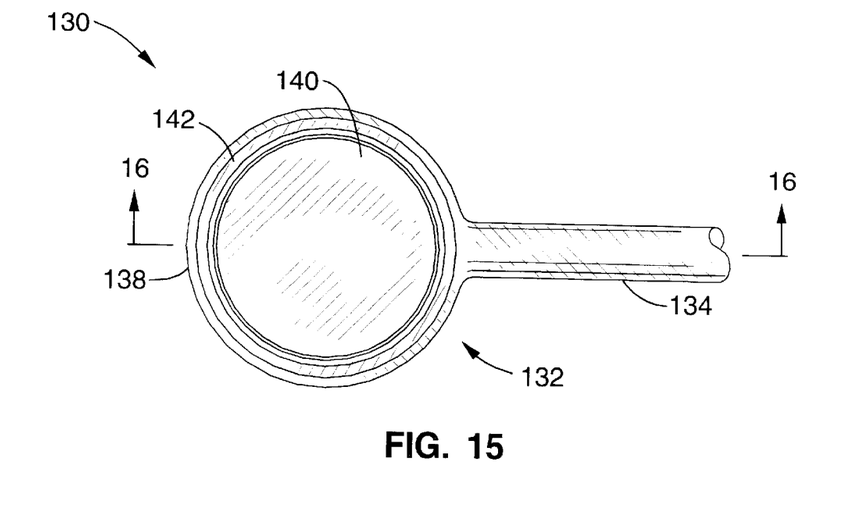
FIG. 15 is a top view of an embodiment of an illuminated mirror according to the present invention utilizing a front-surfaced mirror with a faceted transmissive ring.
Figure 16:
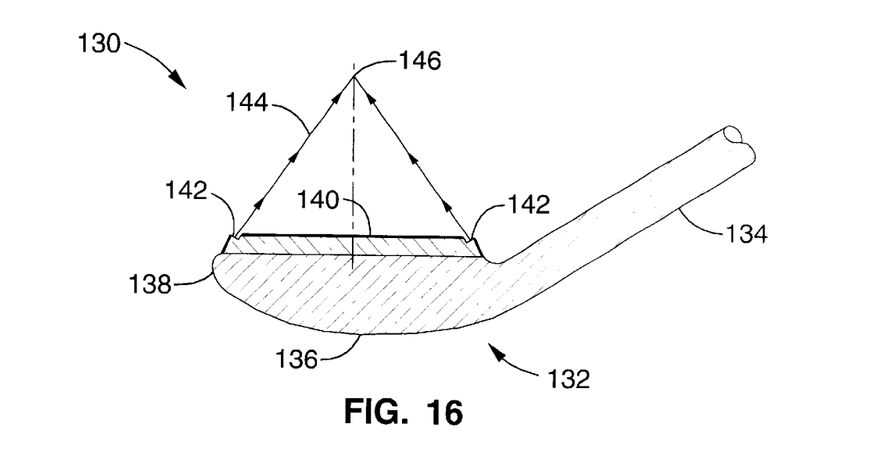
FIG. 16 is a cross-section of the illuminated mirror of FIG. 15 taken through line 16—16.
Figure 17:
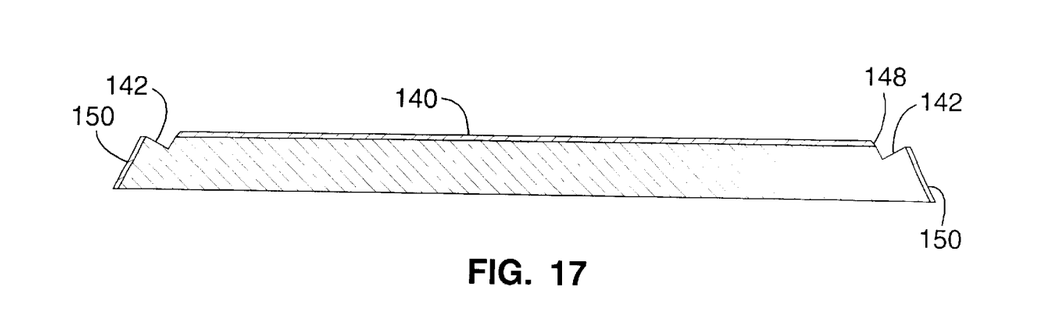
FIG. 17 is a detailed cross-section of the faceted front-surfaced mirror of FIG. 16.

Another embodiment is an illuminating examination mirror 130 of FIG. 15 through FIG. 17, which provides a faceted front-surfaced mirror as a focused light emission surface. The examination mirror 130 has a head 132 connected with a neck 134, bottom surface 136, and edge 138. The mirror 140 within this embodiment is also a front-surfaced mirror, however, rather than being configured with an outward bevel, a faceted ring 142 is cut on its perimeter which focuses the light a specific distance, as determined by the facet angle, above the mirror surface, arrowed lead lines 144 indicate the path of directed light to a point of convergence 146. FIG. 17 illustrates a detailed cross-section exemplifying the mirror 140 shown with facet 142, the front-surface silvering of the mirror 148, and mirror edges 150 adapted for reflection. The edges of the mirror 150 are configured to reflect light, such as by painting, or by the application of silvering, and are angled so as to reflect light received from the head toward the face of the facet 142. The light directed through the neck 134 and head 132 are emitted out the facets of the glass which focuses the light at a given distance above the mirror. A single large faceted ring has been illustrated above, however, it will be appreciated that a number of very fine rings may be provided on the surface of the mirror with each configured having a different facet angle to maintain a single focal point. These concentric rings will be understood to have faceted faces in keeping with Fresnel lens optics. The front-surfaced mirror can be faceted by various conventional means depending on the composition of the mirror, such as molding, etching, and cutting.

Accordingly, it will be seen that the present invention teaches various methods and apparatus for effectively concentrating light above the reflecting surface of an examination mirror trained on a subject area.

Although the description above contains many specificities, these should not be construed as limiting the scope of the invention but as merely providing illustrations of some of the presently preferred embodiments of this invention. Thus the scope of this invention should be determined by the appended claims and their legal equivalents. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An examination mirror, comprising:
   (a) a mirror;
   (b) means for retaining the mirror;
   (c) said means for retaining the mirror configured with at least one slot about a portion of the periphery of the mirror to provide for the peripheral drainage of fluids away from the surface of the mirror;
   (d) means for optically coupling said means for retaining the mirror to a source of illumination; and
   (e) means for directing light received from the source of illumination to the periphery of said means for retaining the mirror and emitting said light about a substantial portion of the perimeter of the mirror to a common location above the surface of said mirror for illuminating a subject area being viewed in the mirror.

2. An examination mirror as recited in claim 1, wherein the mirror has a reflective surface and wherein the light directed about the substantial portion of the perimeter of the mirror is focused at a specified distance above the reflective surface, as determined by the examination application, to facilitate viewing of the subject area within the mirror.

3. An examination mirror as recited in claim 1, wherein the substantial portion of the perimeter spans at least ten percent of the mirror circumference.

4. An examination mirror as recited in claim 1, wherein said means for retaining a mirror comprises a lighted head that fully encircles said mirror and is adapted with a plurality of said slots as drainage apertures distributed about the perimeter of said lighted head.

5. An examination mirror as recited in claim 1, wherein said means for retaining a mirror comprises a lighted head having two arcuate arms separated by said slot, said lighted head adapted to receivably and firmly engage said mirror.

6. An examination mirror as recited in claim 5, wherein a center within said head region is open allowing for both top and bottom surfaces of said mirror to be grasped for removal and insertion therein.

7. An examination mirror as recited in claim 1, wherein said means for retaining a mirror comprises a head assembly having an arcuate section adapted with an annular interior slot aligned for receiving and securely retaining said mirror.

8. An examination mirror as recited in claim 7, wherein said mirror and said annular interior slot are adapted with a corresponding groove and ridge to enhance retention and alignment.

9. An examination mirror, comprising:
   (a) a neck capable of light transmission and further capable of being operatively coupled to a source of illumination; and
   (b) a head having a mirror and a light emitting surface around the periphery of said mirror;
   (c) said head adapted with at least one slot about a portion of the periphery of said mirror through which peripheral drainage of fluids away from the surface of said mirror may be conveyed;
   (d) said head extending from the neck and configured for receiving illumination therefrom, said illumination optically coupled within the head to a light emitting surface which directs light for illuminating a subject area being viewed within the mirror to a focal point above the surface of said mirror.

10. An examination mirror as recited in claim 9, wherein the substantial portion of the perimeter spans at least ten percent of the mirror circumference.

11. An examination mirror as recited in claim 9, wherein said light emitting surface directs the light toward the mirror for reflection toward said focal point above the surface of said mirror.

12. An examination mirror as recited in claim 9, wherein the focal point to which the light from said light emitting surface is focused is a distance above the mirror surface is in the range of approximately one-half inch to two-inches.

13. An examination mirror as recited in claim 9, wherein the mirror is configured to provide the light emitting surface to direct the light from the source of illumination.

14. An examination mirror as recited in claim 9, wherein the mirror held within the head is removably retained.

15. An examination mirror as recited in claim 9, wherein the head and the neck comprise a material which is capable of conducting light energy within any selected portion of the light frequency spectrum lying between the infra-red and the ultraviolet.

16. An examination mirror as recited in claim 9, wherein the mirror may be retained by mechanical or adhesive means.

17. An examination mirror as recited in claim 9, wherein said head fully encircles said mirror and is adapted with a plurality of said slots as drainage apertures distributed about the perimeter of said head.

18. An examination mirror as recited in claim 9, wherein said head comprises two arcuate arms separated by said slot, said head being adapted to receivably and firmly engage said mirror.

19. An examination mirror as recited in claim 18, wherein a center within said head is open allowing for both top and bottom surfaces of said mirror to be grasped for removal and insertion therein.

20. An examination mirror as recited in claim 9, wherein said head comprises an arcuate section adapted with an annular interior slot aligned for receiving and securely retaining said mirror.

21. An examination mirror as recited in claim 20, wherein said mirror and said annular interior slot are adapted with a corresponding groove and ridge to enhance retention and alignment.

22. A lighted examination mirror, comprising:
   (a) a light transmissive shaft;
   (b) a light transmissive head extending from said shaft; and
   (c) a mirror carried by said light transmissive head, said mirror having a perimeter and a reflective surface within said perimeter;
   (d) said head having at least one peripheral slot through which fluids may be conveyed away from said mirror; and
   (e) said head having a light emitting surface surrounding at least a portion of the perimeter of said mirror, wherein rays of light from said light emitting surface are directed to a focal point above the surface of said light transmissive head.

23. A lighted examination mirror as recited in claim 22, wherein said light emitting surface is configured for directing light toward the surface of the mirror for reflection toward said focal point above the surface of said mirror.

24. A lighted examination mirror as recited in claim 23, wherein said mirror is detachable from said head.

25. An examination mirror as recited in claim 22, wherein said light transmissive head fully encircles said mirror and is adapted with a plurality of said slots as drainage apertures distributed about the perimeter of said light transmissive head.

26. An examination mirror as recited in claim 24, wherein said light transmissive head is adapted with two arcuate arms separated by said slot to receivably and firmly engage said mirror, which may be detached from said head.

27. An examination mirror as recited in claim 26, wherein a center within said head is open allowing for both top and bottom surfaces of said mirror to be grasped for removal and insertion therein.

28. An examination mirror as recited in claim 24, wherein said head comprises an arcuate section adapted with an annular interior slot aligned for receiving and detachably retaining said mirror within said head.

29. An examination mirror as recited in claim 28, wherein said mirror and said annular interior slot are adapted with a corresponding groove and ridge to enhance retention and alignment.

30. An examination mirror, comprising:
   (a) a mirror, said mirror having a perimeter and a reflective surface within said perimeter;
   (b) a mirror retainer, said mirror retainer including a light emitting surface surrounding at least a portion of the perimeter of said mirror, said light emitting surface configured to direct light to a common point above the surface of said mirror;
   (c) wherein said mirror retainer is adapted with at least one slot about its periphery through which fluids may be conveyed away from said mirror; and
   (d) a light transmissive shank coupled to said mirror retainer.

31. A lighted examination mirror as recited in claim 30, wherein said light emitting surface is configured for directing light toward the surface of the mirror for reflection toward a focal point above the surface of said mirror.

32. A lighted examination mirror as recited in claim 30, wherein said mirror is detachable from said mirror retainer.

33. An examination mirror as recited in claim 32, wherein said mirror retainer is adapted with two arcuate arms separated by said slot to receivably and firmly engage said mirror, which may be detached from said mirror retainer.

34. An examination mirror as recited in claim 33, wherein a center within said mirror retainer is open allowing for both top and bottom surfaces of said mirror to be grasped for removal and insertion therein.

35. An examination mirror as recited in claim 32, wherein said mirror retainer comprises an arcuate section adapted with an annular interior slot aligned for receiving and detachably retaining said mirror within said mirror retainer.

36. An examination mirror as recited in claim 35, wherein said mirror and said annular interior slot are adapted with a corresponding groove and ridge to enhance retention and alignment.

37. An examination mirror as recited in claim 29, wherein said mirror retainer fully encircles said mirror and is adapted with a plurality of said slots as drainage apertures distributed about the perimeter of said mirror retainer.

38. An examination mirror, comprising:
   a light transmissive shaft;
   a light transmissive head extending from said shaft;
   a mirror carried by said light transmissive head, said mirror having a perimeter and a reflective surface within said perimeter;
   wherein said light transmissive head encircles the perimeter of said mirror and is adapted with a plurality of drainage apertures distributed about said perimeter through which fluids may be conveyed away from said mirror; and
   wherein said light transmissive head is adapted with a light emitting surface surrounding the perimeter of said mirror, wherein rays of light from said light emitting surface are directed to a focal point above the surface of said light transmissive head.

39. An examination mirror, comprising:
   a light transmissive shaft;
   a light transmissive head extending from said shaft and configured with an annular interior slot;
   a mirror engaged within said annular interior slot within said light transmissive head, said mirror having a perimeter and a reflective surface within said perimeter;
   wherein said light transmissive head encircles a first portion of the perimeter of said mirror leaving a second portion of said perimeter of said mirror open as a slot through which fluids may be conveyed away from said mirror; and
   wherein said light transmissive head is adapted with a light emitting surface surrounding said first portion of the perimeter of said mirror, wherein rays of light from said light emitting surface are directed to a focal point above the surface of said light transmissive head.

40. An examination mirror as recited in claim 39, wherein said light transmissive head comprises arcuate arms surrounding a major portion of said mirror and said second portion of said perimeter comprises said slot between said arcuate arms through which fluid may be conveyed.

41. An examination mirror as recited in claim 39, wherein said light transmissive head comprises an arcuate section surrounding a minor portion of said mirror, wherein said second portion of said perimeter comprises said slot, or open region, through which fluid may be conveyed.

42. An examination mirror as recited in claim 41, wherein said annular interior slot in said light transmissive head provides mechanical engagement of said mirror, and allows said mirror to be detached.

43. An examination mirror as recited in claim 42, wherein said annular interior slot and the perimeter of said mirror are adapted with complementary groove and ridge mating surfaces to enhance securement of said mirror.

44. An examination mirror, comprising:

a light transmissive shaft;

a light transmissive head extending from said shaft;

a mirror attached to a front surface of said light transmissive head, said mirror having a transparent rear surface, a perimeter and a reflective front surface within said perimeter;

wherein the perimeter of said mirror is adapted with at least one angled facet relieved within the surface of said mirror, and the elimination of the reflective mirrored surface within said angled facet;

wherein rays of light are directed through said transmissive head through said transparent rear surface of said mirror for being directed by said angled facets of said mirror to a focal point above a central portion of said mirror.

* * * * *